United States Patent [19]

Gallivan et al.

[11] 4,233,465
[45] Nov. 11, 1980

[54] FRACTATION OF OIL OBTAINED BY PYROLYSIS OF LIGNOCELLULOSIC MATERIALS TO RECOVER A PHENOLIC FRACTION FOR USE IN MAKING PHENOL-FORMALDEHYDE RESINS

[75] Inventors: Robert M. Gallivan, Erie, Pa.; Peter K. Mattschei, Plainsboro, N.J.

[73] Assignee: American Can Company, Greenwich, Conn.

[21] Appl. No.: 964,470

[22] Filed: Nov. 29, 1978

Related U.S. Application Data

[62] Division of Ser. No. 918,040, Jun. 22, 1978.

[51] Int. Cl.$^2$ .................. C07C 37/20; C07C 37/28
[52] U.S. Cl. ................................ 568/727; 568/762; 260/29.3
[58] Field of Search .............. 568/727, 762; 260/29.3, 260/25

[56] References Cited

U.S. PATENT DOCUMENTS

| | | | |
|---|---|---|---|
| 1,614,171 | 1/1927 | Amann et al. | 568/727 |
| 2,199,208 | 4/1940 | Owen | 568/762 |
| 2,301,270 | 11/1942 | Gerlicher | 568/762 |
| 2,301,709 | 11/1942 | Remsheidt | 568/762 |
| 2,807,653 | 9/1957 | Filbey et al. | 568/727 |
| 3,093,688 | 6/1963 | Kordzinski | 568/727 |
| 3,277,185 | 10/1966 | Eisenlohr et al. | 568/727 |

*Primary Examiner*—Werren B. Lone
*Attorney, Agent, or Firm*—Robert P. Auber; George P. Ziehmer; Douglas W. Wyatt

[57] ABSTRACT

A method is provided for fractionation of oil obtained by pyrolysis of lignocellulosic materials to obtain useful chemical fractions, including a phenolic fraction which is suitable as a total or partial replacement for phenol in making phenol-formaldehyde resins. The method comprises mixing the oil with a strong base such as sodium hydroxide to a pH level at which the neutral fraction of the oil is selectively soluble in a solvent such as methylene chloride or ether, and the mixture is extracted with the solvent to obtain a first extract containing the solvent and the neutral fraction, and a first raffinate containing the remaining fractions of the oil, i.e., the phenolic fraction, the organic acids fraction and an amorphous residue. The neutral fraction is recovered by distillation and the first raffinate is mixed with sulfuric acid to lower its pH to a level at which the phenolic fraction is selectively soluble in the solvent. This raffinate is extracted with the solvent to obtain a second extract containing the solvent and the phenolic fraction and a second raffinate containing the organic acids and the residues. The phenolic fraction is recovered by distillation and the second raffinate is mixed with sulfuric acid to lower its pH to a level at which the organic acids are selectively soluble in the solvent. After separation of the residues, the second raffinate is extracted with the solvent to obtain a third extract which is distilled to recover the organic acids fraction of the oil. The phenolic fraction may be used as partial or total replacement for pure phenol in making phenol-formaldehyde resins.

13 Claims, 1 Drawing Figure

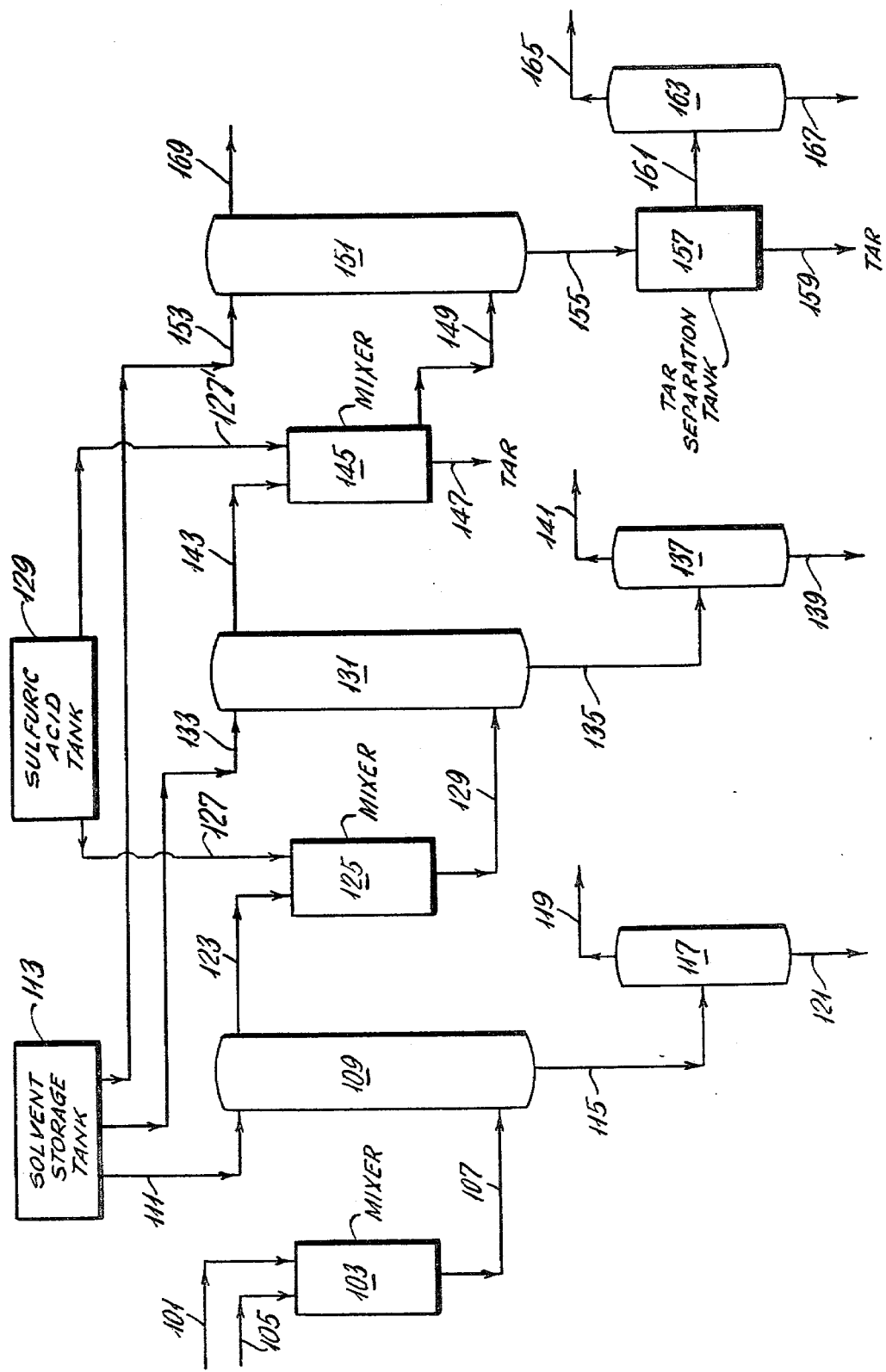

4,233,465

FRACTATION OF OIL OBTAINED BY PYROLYSIS OF LIGNOCELLULOSIC MATERIALS TO RECOVER A PHENOLIC FRACTION FOR USE IN MAKING PHENOL-FORMALDEHYDE RESINS

This is a divisional application of application Ser. No. 918,040 filed June 22, 1978.

BACKGROUND OF THE INVENTION

1. Field of Invention

The present invention relates to a method of fractionation of oil obtained by pyrolysis of lignocellulosic materials, and is particularly related to the fractionation of such oil to recover valuable fractions, including a phenolic fraction. This invention is also concerned with the use of the phenolic fraction obtained from this fractionation to make phenol-formaldehyde resins.

2. The Prior Art

Lignocellulosic wastes such as bark, sawdust, treetops, limbs and the like are pyrolyzed on a commercial scale to obtain a low BTU fuel gas, char for use in making charcoal briquets or activated carbon, and a pyrolytic oil fraction comprising a complex mixture of various chemical compounds presently used as a low cost fuel. Fractionation of the pyrolytic oil yields valuable chemical products, including a phenolic fraction. It has been found that this phenolic fraction can be used as partial or total replacement for pure phenol in making phenol-formaldehyde resins.

Accordingly, it is an object of this invention to provide a method of producing various useful chemicals to replace chemicals currently derived from petroleum.

It is a further object of this invention to derive various useful chemicals from chemical separation of the oily fraction obtained by the pyrolysis of lignocellulosic wastes such as bark, sawdust, treetops, limbs and the like.

It is still another object of this invention to obtain a fraction rich in phenols and polyphenols by chemical fractionation of such pyrolytic oils.

It is also an object of this invention to use the phenolic fraction obtained from fractionation of such pyrolytic oils in making phenol-formaldehyde resins.

The foregoing and other objects of this invention will be more clearly comprehended from the ensuing detailed description of the invention taken in conjunction with the accompanying drawing which is a simplified schematic flow representation of the fractionation method of this invention.

SUMMARY OF INVENTION

In accordance with this invention the oil derived from pyrolysis of lignocellulosic waste materials is first mixed with a strong basic solution such as a sodium hydroxide solution. The resulting black colored mixture with a pH range of from about 11 to about 13 is then contacted with an appropriate solvent such as methylene chloride in a suitable extraction unit. A first extract is recovered from this unit comprising the neutral fraction of the oil which is subjected to distillative operation to remove the solvent and recover the neutral fraction.

The raffinate from this unit is mixed with a mineral acid, such as sulfuric acid, or with carbon dioxide to lower its pH to the range of from about 7.5 to about 9.0, before it is introduced into a second extraction unit wherein it is contacted with a solvent such as methylene chloride. By this extraction step the phenolic fraction is removed with the solvent as the second extract which is distilled to recover the solvent and the phenolic product. The second raffinate from the second extraction unit is mixed with a mineral acid such as sulfuric acid to reduce its pH to the range of from about 1.0 to about 4.0, the tarry residues separated and the mixture is then introduced into a third extraction unit wherein it is contacted with methylene chloride. The third extract from this unit, after the removal of the tarry product is distilled to separate the solvent and recover the organic acids fraction. The third raffinate from the third extraction unit is neutralized and transported to a waste disposal system.

The phenolic fraction obtained by this fractionation method is used as total or partial replacement for petroleum-derived phenol in making phenol-formaldehyde resins. The reaction of formaldehyde with this phenolic fraction is carried out in the presence of a base catalyst, preferably under reflux conditions, until the viscosity of the resulting phenol-formaldehyde polymer reaches about 500 to about 1000 cps.

DETAILED DESCRIPTION OF THE INVENTION

In accordance with this invention the oily fraction obtained by pyrolysis of lignocellulosic waste materials is upgraded by a unique chemical separation or fractionation method to produce four fractions; a neutral fraction, a phenolic fraction, an amorphous residue and a fraction consisting of organic acids. These fractions are obtained by a series of selective extractions or fractionations under carefully controlled conditions and a judicious choice of the extraction solvent.

Thus, according to the method of this invention, and referring to the drawing, the oily fraction obtained from the pyrolysis of lignocellulosic wastes is introduced via conduit 101 into a mixing vessel 103 wherein it is thoroughly mixed with a strong basic solution, such as a dilute solution of sodium hydroxide, which is introduced into the mixer 103 via conduit 105, thereby converting the acidic components of the oil (carboxylic acids and phenols) to their respective salts. The term "lignocellulosic waste" employed herein is intended to include bark, sawdust, treetops, limbs, and the like, or mixtures thereof. Moreover, while sodium hydroxide is the alkali of choice, other bases such as potassium hydroxide and ammonium hydroxide may be employed efficaciously and in varying concentrations.

The amount of sodium hydroxide used to convert the acidic components of the oil into their respective salts must be sufficient to result in a mixture having a pH of from about 11 to about 13. At his pH range, the neutral components of the oil are selectively soluble in the solvents employed in the practice of this invention.

The oil-base mixture from mixer 103 is then introduced via conduit 107 into a fractionation or extraction column 109 wherein it is contacted with a solvent introduced into the column 109 via conduit 111 emanating from a solvent storage tank 113. The solvents which are particularly effective for the removal of the neutral fractions of the oil in the practice of this invention are methylene chloride, ether, chloroform, butanol and hydrocarbon solvents.

The relative volumetric flow rates of the solvent to the oil-base mixture may vary from about 3:1 to about 1:1. The temperature at which the extraction of the neutral fraction of the oil is carried out depends, to a great extent, on the boiling point of the solvent. In general, and for the solvents employed herein, this extraction step may be conveniently carried out at ambient temperatures.

The extract from column 109 is withdrawn via conduit 115 and introduced into a distillation column 117 wherein the solvent is recovered by steam distillation, or any other suitable method, and removed from the column 117 via conduit 119. It may be cooled and condensed and returned to the solvent storage tank 113, if desired. The extract which is withdrawn from distillation column 117 via conduit 121 consists of the neutral fraction of the oil. This fraction may be stored in a storage vessel (not shown) for further use.

The raffinate from the extraction column 109 is withdrawn via conduit 123 and introduced into a mixing vessel 125 wherein it is mixed with a 50% sulfuric acid solution introduced into the mixing vessel 125 via conduit 127 withdrawn from an acid storage tank 129. The raffinate from column 109 is mixed with sufficient amount of sulfuric acid in the mixer 125 until the pH of the resulting mixture is within the range of from about 7.5 to 9.0. It has been found that at this pH range, the phenolic fraction of the oil is selectively soluble in the solvents employed in the practice of this invention. Thus, the raffinate from column 109, after thorough mixing and pH adjustment in mixer 125, is withdrawn from the mixer 125 via conduit 129 and introduced into a second extraction or fractionation column 131 wherein it is contacted with the solvent introduced into the column 131 via conduit 133 from the solvent storage tank 113.

The relative volumetric flow rates of the solvent and the feed in column 131 may vary from about 3:1 to about 1:1. Once again, the extraction temperature in column 131 depends on the boiling point of the solvent but, in general, ambient temperatures are quite satisfactory.

The extract from column 131 is withdrawn via conduit 135 and distilled in the presence of steam in distillation column 137 to recover the phenolic fraction via conduit 139. The solvent is removed overhead via conduit 141, cooled and condensed, and may be returned to the solvent storage tank 113, if desired.

The raffinate from the fractionation column 131 is withdrawn via conduit 143, introduced into a mixing vessel 145 wherein it is mixed with sufficient quantity of a 50% sulfuric acid solution withdrawn from the acid tank 129, and introduced into the mixer 145 via conduit 127', until the pH of the resulting mixture is in the range of from about 1.0 to about 4.0. After separating a tarry residue via conduit 147, the mixture from mixer 145 is withdrawn via conduit 149 and fed to a third fractionation or extraction column 151 wherein the mixture is contacted with the solvent withdrawn from solvent storage tank 113 and introduced into the column 151 via conduit 153.

Once again the relative volumetric flow rates of the solvent and the feed in column 151 may vary from about 3:1 to about 1:1. The optimum temperature for the extraction of the organic acids fraction of the oil in column 151 depends on the boiling point of the solvent, and again, ambient temperatures have been found to be quite satisfactory.

The extract from column 151 is withdrawn via conduit 155 and introduced into a separation tank 157 wherein tarry products are separated and withdrawn via conduit 159 and the tar-free mixture introduced via conduit 161 to a distillation column 163 wherein the mixture is steam distilled to remove the solvent overhead via conduit 165, cooled and condensed, and returned to the solvent storage tank, if desired. The extract from the distillation column 163, which is withdrawn via conduit 167, consists basically of the organic acids fraction of the oil.

The raffinate from column 151 which is withdrawn via conduit 169 may be conveyed to a neutralization and disposal tank (not shown).

The following examples will serve to further illustrate the fractionation method of this invention. Methylene chloride was the solvent employed in one example and ether was the solvent employed in the other example. The same standard laboratory equipment were used in both examples, except that the extraction column in the example using methylene chloride was different from the extraction column in the example using ether. It must be understood, however, that these examples are merely intended to further illustrate the practice of this invention without in any way limiting its scope.

EXAMPLE I

One hundred milliliters (99.28 grams dry weight) of distillate oil and 300 ml. of 10% sodium hydroxide (30 grams NaOH) were mixed thoroughly to obtain a black mixture having a pH of 11. The distillate oil employed in this example was derived from the pyrolysis of sawdust and had a density of 1.082 gm/cc, a pH of 2.60 and contained 14.3% water. The black mixture was charged to a 1 liter continuous liquid-liquid extraction column equipped with an overhead condenser and a flask, and the mixture was extracted with methylene chloride at 70° F. until a clear solution was obtained. The contents of the extraction column were then transferred to a 2 liter separatory funnel wherein it was allowed to separate into an organic bottom layer and a top aqueous layer. The organic bottom layer was transferred to the extract in the boiling flask and dried with anhydrous sodium sulfate, and the solvent was then stripped off on a rotary evaporator to obtain 32.8 grams of a dark brown, viscous oil constituting the neutral fraction.

The alkaline aqueous phase which had a pH of 10.2 was mixed with dry ice to lower its pH to 7.8 and, 500 ml. of water was added thereto and the mixture transferred to a 2 liter extractor and contacted with methylene chloride at 70° F. and then transferred to a 2 liter separatory funnel. The bottom solvent layer from the separatory funnel was combined with the extract from the boiling flask and dried with anhydrous sodium sulfate, and the solvent was stripped off on a rotary evaporator to obtain 21.77 grams of a black, highly viscous product constituting the phenolic fraction of the wood waste distillate oil.

The alkaline aqueous phase was treated with 75 ml. of a 50% sulfuric acid solution to reduce its pH from 9 to 2 resulting in some tar separation. The acidic phase was transferred to a 2 liter liquid-liquid extractor wherein it was contacted with methylene chloride at 70° F., and the contents of the extractor were transferred to a 2 liter separatory funnel. The bottom solvent layer from the separatory funnel was combined with the extract in the boiling flask and dried with anhydrous sodium sulfate, and the solvent was stripped off on a rotary evaporator to obtain 9.41 grams of an amber color oil representing the organic acid fraction of the oil.

The black tar recovered in the previous step was subjected to azeotropic distillation with toluene and the black solid product formed in this distillation was separated from toluene and dried to obtain 16.5 grams of a dark brown, amorphous product.

The toluene solution was stripped off on a rotary evaporator and yielded 2.30 grams of a brown semi-solid material which constituted an additional quantity of organic acids. In an alternative procedure, the black tar is digested in hot water, separated by filtration and dried to give a dark brown amorphous solid.

Table I below summarizes the yields of the various fractions obtained in this Example.

TABLE I

| Fraction | Weight gm | Water % | Dry Weight gm | Yield % |
|---|---|---|---|---|
| Distillate Oil | 115.84 | 14.3 | 99.28 | — |
| Neutrals | 33.05 | 0.76 | 32.80 | 33.04 |
| Phenols | 21.92 | 0.67 | 21.77 | 21.93 |
| Acids | 9.56 | 1.53 | 9.41 | 9.48 |
| Residues | 16.74 | 2.32 | 18.65 | 18.79 |
| Total Recovery | | | | 83.24 |

EXAMPLE II

One hundred and fifty milliliters of distillate oil (117.26 grams on dry weight basis) was thoroughly mixed with 300 ml. of 25% sodium hydroxide solution (75 grams NaOH) to obtain a black mixture having a pH of 11.96. The source of the distillate oil was the same as that used in Example I. The black mixture was then transferred to a 1 liter continuous liquid-liquid extractor and contacted therein with ether at 70° F. until a clear solution was obtained. The contents of the extractor were transferred to a separatory funnel and allowed to separate, and the bottom aqueous layer was drained into a beaker and set aside. The top organic phase was combined with the extract from the boiling flask and dried over anhydrous sodium sulfate, and the solvent was stripped off on a rotary evaporator to yield 37.79 grams of dark brown oil which constitutes the neutral fraction of the wood wastes distillate oil. Upon standing, crystalline solids separated out from this fraction.

The aqueous layer which was set aside was mixed with a 50% sulfuric acid solution until its pH was reduced from 13.75 to 7.90, and the resulting black mixture was transferred to the extractor and contacted with ether at 70° F. After completion of the extraction, the contents of the extractor were transferred to a separatory funnel wherein two layers were formed; a bottom aqueous layer which was drained into a beaker and set aside, and a top organic layer which was combined with the extract in the boiling flask, dried with anhydrous sodium solfate and the solvent stripped off on a rotary evaporator. 38.72 grams of a thick black oil was obtained representing the phenolic fraction of the distillate oil.

The aqueous phase was mixed with 150 ml. of a 50% sulfuric acid solution to lower its pH to 2 and the mixture was transferred to the extractor wherein it was contacted with ether at 70° F. The contents of the extractor were then transferred to a separatory funnel wherein a black tar separated out which was removed and set aside. The bottom aqueous phase from the funnel was discarded and the top organic layer was combined with the extract from the boiling flask, dried with sodium sulfate, and the solvent stripped off on a rotary evaporator to yield 28.19 grams of a brown oil which represents the organic acid fraction of the wood waste distillate oil.

The tar obtained in the previous step was dehydrated by azeotropic distillation with toluene to yield 4.76 grams of a dark brown solid. In an alternative procedure, the black tar is digested in hot water, separated by filtration and dried to give a dark brown amorphous solid.

The yields of various fractions obtained in this example are shown in Table II below.

TABLE II

| Fraction | Weight gm | Water % | Dry Weight gms | Yield % |
|---|---|---|---|---|
| Distillate Oil | 136.82 | 14.3 | 117.26 | — |
| Neutrals | 40.60 | 6.92 | 37.79 | 32.23 |
| Phenols | 20.66 | 4.76 | 38.72 | 33.02 |
| Acids | 36.72 | 23.23 | 28.19 | 24.04 |
| Residues | 4.95 | 3.93 | 4.76 | 4.06 |
| Total Recovery | | | | 93.35 |

From the foregoing description it is evident that this invention provides a unique method of upgrading distillate oil to provide various chemical fractions, including a phenolic fraction.

A combination of gas chromatographic and infrared spectroscopic characterization of the phenolic fraction obtained by the method of this invention revealed the presence of phenol, o-cresol, p-cresol, guaicol, 4-methyl guaicol, 4-ethyl guaicol, isoeugenol, eugenol, a benzophenone derivative and delignol.

The organic acids fraction obtained by the fractionation method of this invention includes acetic acid, propionic acid, butyric acid and other higher acids.

The fractionation of distillate oil in accordance with this invention may be carried out continuously, semi-continuously or in a batchwise manner using readily available equipment and reagents. The solvent extraction step may be carried out concurrently or countercurrently, although countercurrent, liquid-liquid extraction constitutes the preferred practice, since it is more efficient and is readily adaptable to large scale industrial operation.

While in the foregoing description the invention has been described in detail, and with certain degrees of particularity, it is evident to those skilled in the art that several changes and modifications may be made which are suggested from the detailed disclosure herein, and which are nevertheless contemplated by, and obvious from the description of this invention. For example, and in a different embodiment of the invention, the oil may be first dissolved in the solvent and the resulting solution treated with 10% sodium hydroxide solution until the pH of the mixture is from about 11 to about 13. This treatment results in an organic phase containing the neutral fraction of the oil and an aqueous phase containing the remaining fractions. The organic phase may be distilled to recover the neutral fractions, and the aqueous phase is treated with sulfuric acid or gaseous carbon dioxide to reduce its pH to the range of from about 8 to about 8.5, and thereafter subjected to a series of extractive and distillative operations, essentially as described in connection with the previous embodiment, in order to recover the phenolic fraction and the acids fraction of the oil.

Example III below illustrates this embodiment of the invention.

EXAMPLE III

Five hundred and two grams of filtered distillate oil obtained from pyrolysis of a mixture of bark and sawdust was dissolved in 1250 ml. of methylene chloride and the resulting solution was separated from the insolubles. The insolubles were then extracted with several portions of methylene chloride to give 106 grams of insoluble oil. The resulting solution and the extract were combined and treated 3 times with 460 ml. of 10% sodium hydroxide in an ice bath and the organic phase was dried and evaporated to give 129 grams of neutral fraction, corresponding to a yield of 31%.

The combined aqueous phase with a pH of 12.3 was treated with gaseous carbon dioxide to lower its pH to 8. This aqueous phase was extracted several times with methylene chloride, and the organic phase was dried and evaporated to give 139 gm. of phenolic fraction, corresponding to a yield of 33%. The aqueous phase was acidified with 280 ml. of 10% sulfuric acid to a pH of 2 and extracted several times with methylene chloride, and the resulting solids were filtered off to give 7 gm. of organic acids. The combined organic layers were then dried and evaporated to give an additional 12 grams of organic acids, corresponding to a combined yield of 5%.

As it was previously mentioned, the phenolic fraction obtained by the fractionation of lignocellulosic waste materials as hereinbefore described can be employed as partial or total replacement for petroleum-derived phenol in the synthesis of phenol-formaldehyde resins. Since these phenolic fractions contain substantial amounts of polyphenolic compounds, the resulting phenol-formaldehyde resins are highly cross-linked polymers.

Thus, phenol-formaldehyde resins may be made by reacting formaldehyde with the phenolic fraction in the presence of a base catalyst such as sodium hydroxide, preferably under reflux conditions, until the viscosity of the resulting phenol-formaldehyde polymer is in the range of from about 500 cps to about 1000 cps. While such phenolic fractions may be used as total replacement for petroleum-derived phenol, it is generally recommended that the phenolic reactant contains from about 25 to about 75 weight percent phenolic fraction obtained from fractionation of such distillate oils, with the remainder being petroleum-derived phenol.

EXAMPLE IV

Twenty five grams of a phenolic fraction obtained from the fractionation of distillate oil obtained by pyrolysis of a mixture of sawdust and bark was mixed with 25 grams of petroleum-derived phenol, 87 grams of 37% formaldehyde solution, 13 grams of 50% sodium hydroxide solution and 60 ml. of water. The mixture was then transferred to a 500 ml. reaction flask equipped with a stirrer, reflux condenser and a thermometer and reacted under reflux conditions for 25 minutes. Thereafter an additional 15 grams of a 50% sodium hydroxide solution was added to the content of the reaction flask and the resulting mixture was refluxed for another 25 minutes. After this period, an additional 15 grams of a 50% sodium hydroxide solution was added to the reaction flask and the mixture was refluxed for another 30 minutes. The viscosity of the resulting resin at this state was determined by a Wells-Brookfield Micro Viscometer to be 208 cps. The reaction mixture was further refluxed for an additional 25 minutes to obtain 209 grams of finished resin representing a yield of 87 weight percent. The viscosity of the finished resin was determined to be 662 cps.

The phenol-formaldehyde resins made by the reaction described herein may be used to make adhesive preparations which may be used for lamination plywood. Thus, 60 grams of the phenol-formaldehyde resin made as in Example IV was mixed in a beaker with 12 grams of Furafil (made by Quaker Oats Co.), 6 grams of 50% solution of sodium hydroxide and 22 grams of water to make an adhesive having a viscosity of 343 cps. The resulting adhesive was used to laminate veneer panels which were tested for wood failure. The results obtained by using adhesives made from phenol-formaldehyde resins made as in Example IV were comparable to the results obtained with adhesives made from phenol-formaldehyde resins using petroleum derived phenols.

What is claimed is:

1. A method of recovering a phenolic fraction from distillate oil obtained by pyrolysis of lignocellulosic waste materials, and making phenol-formaldehyde resins therefrom which comprises:
    (a) mixing said oil with a base selected from the group consisting of sodium hydroxide, potassium hydroxide and ammonium hydroxide to obtain a mixture having a pH in the range of from about 11 to about 13;
    (b) contacting said mixture, in a first extraction zone, with a solvent selected from the group consisting of ether, methylene chloride, chloroform, butanol and hydrocarbons, wherein the volumetric flow rates of the solvent to said mixture is from about 3:1 to about 1:1 to thereby selectively extract the neutral fraction of said oil;
    (c) removing a first extract and a first raffinate from said first extraction zone and recovering the neutral fraction from said first extract;
    (d) mixing said first raffinate with a mineral acid or carbon dioxide until the pH of said raffinate is lowered to the range of from about 7.5 to about 9.0 and contacting the resulting mixture with said solvent in a second extraction zone, wherein the volumetric flow rates of the solvent to said mixture is from about 3:1 to about 1:1, to thereby selectively extract the phenolic fraction of said oil;
    (e) removing a second extract containing said phenolic fraction, and a second raffinate from said second extraction zone,
    (f) recovering said phenolic fraction from said second extract, and
    (g) reacting said phenolic fraction with formaldehyde in the presence of a metal hydroxide catalyst until the viscosity of the resulting phenol-formaldehyde resin reaches from about 500 cps to about 1000 cps.

2. A method as in claim 1 wherein said reaction is carried out under reflux conditions.

3. A method as in claim 1 wherein said catalyst is sodium hydroxide.

4. A method as in claim 2 wherein said catalyst is sodium hydroxide.

5. A method of making phenol-formaldehyde resin which comprises reacting formaldehyde with the phenolic fraction recovered from fractionation of distillate oil obtained by pyrolysis of lignocellulosic waste materials, said reaction being carried out in the presence of a metal hydroxide catalyst until the viscosity of the resulting phenol-formaldehyde resin reaches from about 500 cps to about 1000 cps.

6. A method as in claim 5 wherein said reaction is carried out under reflux conditions.

7. A method as in claim 5 wherein said catalyst is sodium hydroxide.

8. A method as in claim 6 wherein said catalyst is sodium hydroxide.

9. A method of recovering a phenolic fraction from distillate oil obtained by pyrolysis of lignocellulosic waste materials and making phenol-formaldehyde resins therefrom which comprises:
  (a) dissolving said oil in a solvent selected from the group consisting of ether, methylene chloride, chloroform, butanol and hydrocarbons;
  (b) treating the resulting solution with a base selected from the group consisting of sodium hydroxide, potassium hydroxide and ammonium hydroxide, wherein the amount of said base is calculated to produce a mixture having a pH of from about 11 to about 13 to thereby obtain an organic phase containing the neutral fraction of said oil and an aqueous phase containing the phenolic fraction and acids fraction of said oil;
  (c) separating said aqueous phase and mixing it with a mineral acid or gaseous carbon dioxide until its pH is lowered to the range of from about 7.5 to about 9.0 and contacting the resulting mixture with said solvent in an extraction zone to selectively extract the phenolic fraction of said oil;
  (d) removing an extract containing said phenolic fraction and recovering said phenolic fraction from said extract; and
  (e) reacting said phenolic fraction with formaldehyde in the presence of a metal hydroxide catalyst until the viscosity of the resulting phenol-formaldehyde resin reaches from about 500 cps to about 1000 cps.

10. A method as in claim 9 wherein said phenolic fraction is recovered by distillation.

11. A method as in claim 9 wherein said reaction is carried out under reflux conditions.

12. A method as in claim 9 wherein said catalyst is sodium hydroxide.

13. A method as in claim 11 wherein said catalyst is sodium hydroxide.

* * * * *